United States Patent
Karnieli et al.

(10) Patent No.: US 10,251,389 B2
(45) Date of Patent: Apr. 9, 2019

(54) METHOD AND DEVICE FOR THAWING BIOLOGICAL MATERIAL

(71) Applicant: Pluristem Ltd., Haifa (IL)

(72) Inventors: Ohad Karnieli, Tivo'on (IL); Tal Slonim, Rishon Le Zion (IL); Lior Raviv, Kfar Monash (IL); Nufar Gross, Haifa (IL)

(73) Assignee: PLURISTEM LTD., Haifa (IL)

( * ) Notice: Subject to any disclaimer, the term of this patent is extended or adjusted under 35 U.S.C. 154(b) by 502 days.

(21) Appl. No.: 14/597,505

(22) Filed: Jan. 15, 2015

(65) Prior Publication Data

US 2015/0125138 A1    May 7, 2015

Related U.S. Application Data

(63) Continuation-in-part of application No. PCT/IB2013/059808, filed on Oct. 31, 2013.

(Continued)

(51) Int. Cl.
*F24H 1/18* (2006.01)
*A01N 1/02* (2006.01)
(Continued)

(52) U.S. Cl.
CPC ......... *A01N 1/0284* (2013.01); *A01N 1/0242* (2013.01); *B01L 7/00* (2013.01);
(Continued)

(58) Field of Classification Search
None
See application file for complete search history.

(56) References Cited

U.S. PATENT DOCUMENTS 2,741,099 A * 4/1956 Beane .................. F25D 29/008
                                                          340/585
3,518,393 A * 6/1970 Bull ...................... A61M 5/445
                                                          219/772

(Continued)

FOREIGN PATENT DOCUMENTS

| CN | 1582111 A | 2/2005 |
|---|---|---|
| EP | 2510965 A1 | 10/2012 |

(Continued)

OTHER PUBLICATIONS

[No Author Listed] Torrey Pines Scientific, Inc. 2008 Catalog. Temperature Control Specialists. Jan. 1, 2008 . Last accessed at http://www.hohoteco.idv.tw/Files/TPSCatalog2008.pdf on Jun. 18, 2014. 24 pages.

(Continued)

*Primary Examiner* — Thor S Campbell
(74) *Attorney, Agent, or Firm* — Lando & Anastasi, LLP

(57) ABSTRACT

This disclosure is a system for heating a sample, e.g. a biological material, in a vessel. The system can include a heating device configured to transmit energy to the vessel and a base moveably coupled to the heating device. The system can also include a processor configured to receive an input associated with a target temperature, and transmit a signal to controllably move the heating device relative to the base for a time period, wherein the time period is determined based on the target temperature and content volume.

35 Claims, 14 Drawing Sheets

Related U.S. Application Data

(60) Provisional application No. 61/720,552, filed on Oct. 31, 2012.

(51) Int. Cl.
  *B01L 7/00* (2006.01)
  *H05B 1/02* (2006.01)
  *B01F 9/00* (2006.01)
  *C12M 1/00* (2006.01)

(52) U.S. Cl.
  CPC .............. *H05B 1/02* (2013.01); *B01F 9/0014* (2013.01); *B01L 2200/147* (2013.01); *B01L 2300/1827* (2013.01); *B01L 2300/1861* (2013.01); *B01L 2400/0409* (2013.01); *C12M 47/20* (2013.01)

(56) References Cited

U.S. PATENT DOCUMENTS

| | | | | |
|---|---|---|---|---|
| 4,167,663 A * | 9/1979 | Granzow, Jr. | ........... | A61M 5/44 219/497 |
| 4,189,995 A * | 2/1980 | Lohr | ........... | F24C 15/327 126/21 A |
| 4,336,435 A * | 6/1982 | Kashyap | ........... | H05B 6/64 219/687 |
| 4,473,739 A | 9/1984 | Scheiwe et al. | | |
| 4,481,410 A * | 11/1984 | Bortnick | ........... | A61L 12/04 219/386 |
| 4,495,402 A * | 1/1985 | Burdick | ........... | A47J 27/004 219/214 |
| 4,625,096 A * | 11/1986 | Fletcher | ........... | B01L 7/02 392/441 |
| 4,652,712 A * | 3/1987 | Zeipel | ........... | A61M 5/445 219/687 |
| 4,714,813 A * | 12/1987 | Trenchard | ........... | B01F 9/0001 219/687 |
| 4,742,202 A * | 5/1988 | Campbell | ........... | H05B 6/64 219/687 |
| 4,801,777 A * | 1/1989 | Auerbach | ........... | A61M 5/445 219/687 |
| 4,855,555 A * | 8/1989 | Adams | ........... | H05B 6/64 219/753 |
| 4,874,915 A * | 10/1989 | Harms | ........... | A61M 5/445 219/759 |
| 4,906,816 A * | 3/1990 | van Leerdam | ........... | A61M 5/44 392/470 |
| 4,956,532 A | 9/1990 | Koch | | |
| 5,061,630 A * | 10/1991 | Knopf | ........... | B01L 7/52 422/500 |
| 5,081,697 A * | 1/1992 | Manella | ........... | A61M 5/44 392/481 |
| 5,243,833 A * | 9/1993 | Coelho | ........... | A61M 5/445 165/104.28 |
| 5,250,032 A * | 10/1993 | Carter, Jr. | ........... | A61M 5/44 219/535 |
| 5,282,264 A * | 1/1994 | Reeves | ........... | F26B 19/005 219/385 |
| 5,297,234 A * | 3/1994 | Harms | ........... | A23L 3/365 392/379 |
| 5,374,811 A * | 12/1994 | Kiel | ........... | A61M 5/445 219/687 |
| 5,658,478 A * | 8/1997 | Roeschel | ........... | F24C 3/126 219/502 |
| 5,989,238 A * | 11/1999 | Ginsburg | ........... | A61M 5/445 604/113 |
| 6,007,773 A * | 12/1999 | Kuzyk | ........... | A61M 5/445 165/104.31 |
| 6,077,447 A * | 6/2000 | Coelho | ........... | B01L 7/00 210/175 |
| 6,175,099 B1 * | 1/2001 | Shei | ........... | A47J 39/006 219/385 |
| 6,259,067 B1 * | 7/2001 | Faries, Jr. | ........... | A61B 50/10 219/394 |
| 6,294,762 B1 * | 9/2001 | Faries, Jr. | ........... | A61F 7/0241 126/21 A |
| 6,566,631 B2 * | 5/2003 | Faries, Jr. | ........... | G01K 11/12 219/386 |
| 6,653,605 B2 * | 11/2003 | Kneuer | ........... | A61G 11/00 219/217 |
| 6,748,164 B1 * | 6/2004 | Kuzyk | ........... | A61M 1/0281 392/443 |
| 6,768,085 B2 * | 7/2004 | Faries, Jr. | ........... | A61M 5/445 219/385 |
| 7,011,797 B2 * | 3/2006 | Bakke | ........... | A61M 1/025 219/200 |
| 7,025,877 B1 * | 4/2006 | de Gheldere | ........... | A61J 1/10 210/202 |
| 7,068,361 B2 * | 6/2006 | Cimino | ........... | A61L 2/0011 356/213 |
| 7,307,245 B2 * | 12/2007 | Faries, Jr. | ........... | G06F 19/00 219/413 |
| 7,722,839 B2 * | 5/2010 | Kuzyk | ........... | A01N 1/0242 100/269.04 |
| 8,012,416 B2 * | 9/2011 | Kuzyk | ........... | H05B 3/82 392/443 |
| 8,362,402 B2 * | 1/2013 | Hansen | ........... | A61M 5/445 219/385 |
| 8,366,655 B2 * | 2/2013 | Kamen | ........... | A61M 1/1037 604/29 |
| 8,821,011 B2 * | 9/2014 | Faries, Jr. | ........... | G01K 11/12 374/141 |
| 9,119,912 B2 * | 9/2015 | Faries, Jr. | ........... | A61M 5/445 |
| 9,173,248 B2 * | 10/2015 | Baker | ........... | H05B 1/025 |
| 9,656,029 B2 * | 5/2017 | Tsang | ........... | A61M 5/44 |
| 2002/0147426 A1 * | 10/2002 | Faries, Jr. | ........... | A61M 5/1483 604/140 |
| 2006/0013063 A1 * | 1/2006 | Singh | ........... | B01F 11/0017 366/239 |
| 2006/0063122 A1 | 3/2006 | Heeg et al. | | |
| 2006/0153549 A1 * | 7/2006 | Cazzini | ........... | A61M 5/445 392/470 |
| 2008/0253754 A1 * | 10/2008 | Rubin | ........... | A45D 20/12 392/381 |

FOREIGN PATENT DOCUMENTS

| | | |
|---|---|---|
| JP | H07165592 A | 6/1995 |
| JP | H07293898 A | 11/1995 |
| JP | 2006004299 A | 1/2006 |
| JP | 2007535902 A | 12/2007 |
| JP | 2009118845 A | 6/2009 |
| RU | 20243 U1 | 10/2001 |
| WO | 0045953 A1 | 8/2000 |

OTHER PUBLICATIONS

[No Author Listed] Exhibit D4 as cited in corresponding European Application No. 13844536.6 on Apr. 30, 2018, 1 page.

International Search Report and Written Opinion issued in PCT/IB2013/059808, dated Jun. 30, 2014.

\* cited by examiner

METHOD AND DEVICE FOR THAWING BIOLOGICAL MATERIAL

RELATED APPLICATIONS

This Application is a continuation-in-part of International Application PCT/IB2013/059808 filed on Oct. 31, 2013, which claims the benefit of U.S. Provisional Application 61/720,552 filed on Oct. 31, 2012. The entire contents of these applications are incorporated herein by reference in thier entirety.

FIELD OF THE TECHNOLOGY

The present disclosure relates to a heating device and, more particularly, to systems and methods for thawing biological material.

BACKGROUND

Various biological materials are typically stored below freezing. For long-term storage, cells, peptides, or nucleic acids can be stored at −80° C., −20° C., or in liquid nitrogen at −195° C. Short-term storage can include temperatures at or greater than 0° C.

Many biological experiments are typically conducted at temperatures greater than these storage temperatures. For example, eukaryotic cells are often grown at 37° C., while prokaryotic cells often prefer different temperatures.

Traditionally, biological materials are aliquoted in vials and frozen for storage. To heat these vials, a person would usually take each vial and place it in a hot water bath. The person would carefully stir the vial in the bath to ensure uniform heating of the vials contents and to swirl the biological material within the vial. After some time, the person would remove the vial from the water bath and determine if the contents had sufficiently thawed. Once properly thawed, the biological material would be ready for use.

Several problems exist with traditional heating protocols. Firstly, the chance of contamination is high, as multiple vials are usually placed in the same water bath. To ensure sterility, the vial is typically wiped with an ethanol solution following removal from the water bath. However, the wipe may not be completely effective, and contaminants may remain on the vial or cap surface.

Secondly, the heating process may not be repeatable from vial to vial, as operators introduce human variability. Heating times, swirling duration, swirling speed, etc. may all vary significantly. Because some biological materials are sensitive to differing thermal gradients, shear forces, or agitation levels, experimental outcomes can be affected.

Thirdly, tracking vials using traditional water baths can be difficult. Labels can be removed by the warm water, and markings on the vials can be inadvertently removed by the ethanol wipe.

Finally, thawing may not include uniform heat dispersion. If a portion of material thaws and is not mixed correctly, refreezing may occur. Refreezing can cause re-crystallization and damage cells. An improved thawing device should be optimized to reduce non-uniform thawing and re-crystallization. Accordingly, there is a need for systems and methods to better thaw biological materials.

SUMMARY OF THE DISCLOSURE

One embodiment consistent with the principles of this disclosure is a method for thawing a frozen biological material. The steps can include setting a target temperature for the biological material and applying heat to the biological material via a heating device, which is, in some embodiments, a component of a system. The method can also include controllably moving the heating device for a specific time period, wherein the time period is determined based on the target temperature, the vial content material, and the content volume. Moving the heating device serves to move the biological material, which was originally frozen and is being heated, and thus thawed or in the process of being thawed, while in motion.

Another embodiment of this disclosure is directed to a system for heating a biological material in a vessel (e.g. a vial, tube, or other container). The system can include a heating device configured to transmit energy to the vessel and a base moveably coupled to the heating device. The system can also include a processor configured to receive an input associated with a target temperature, and transmit a signal to controllably move the heating device relative to the base for a time period, wherein the time period is determined based on the target temperature and the content volume.

Additional embodiments consistent with principles of the disclosure are set forth in the detailed description which follows or may be learned by practice of methods or use of systems or articles of manufacture disclosed herein. It is understood that both the foregoing general description and the following detailed description are exemplary and explanatory only, and are not restrictive of the disclosure as claimed. Additionally, it is to be understood that other embodiments may be utilized and that electrical, logical, and structural changes may be made without departing from the spirit and scope of the present disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure. In the drawings.

DESCRIPTION OF THE EMBODIMENTS

Reference will now be made in detail to the present embodiments of the disclosure, examples of which are illustrated in the accompanying drawings. Wherever possible, the same reference numbers will be used throughout the drawings to refer to the same or like parts.

Figure 1:
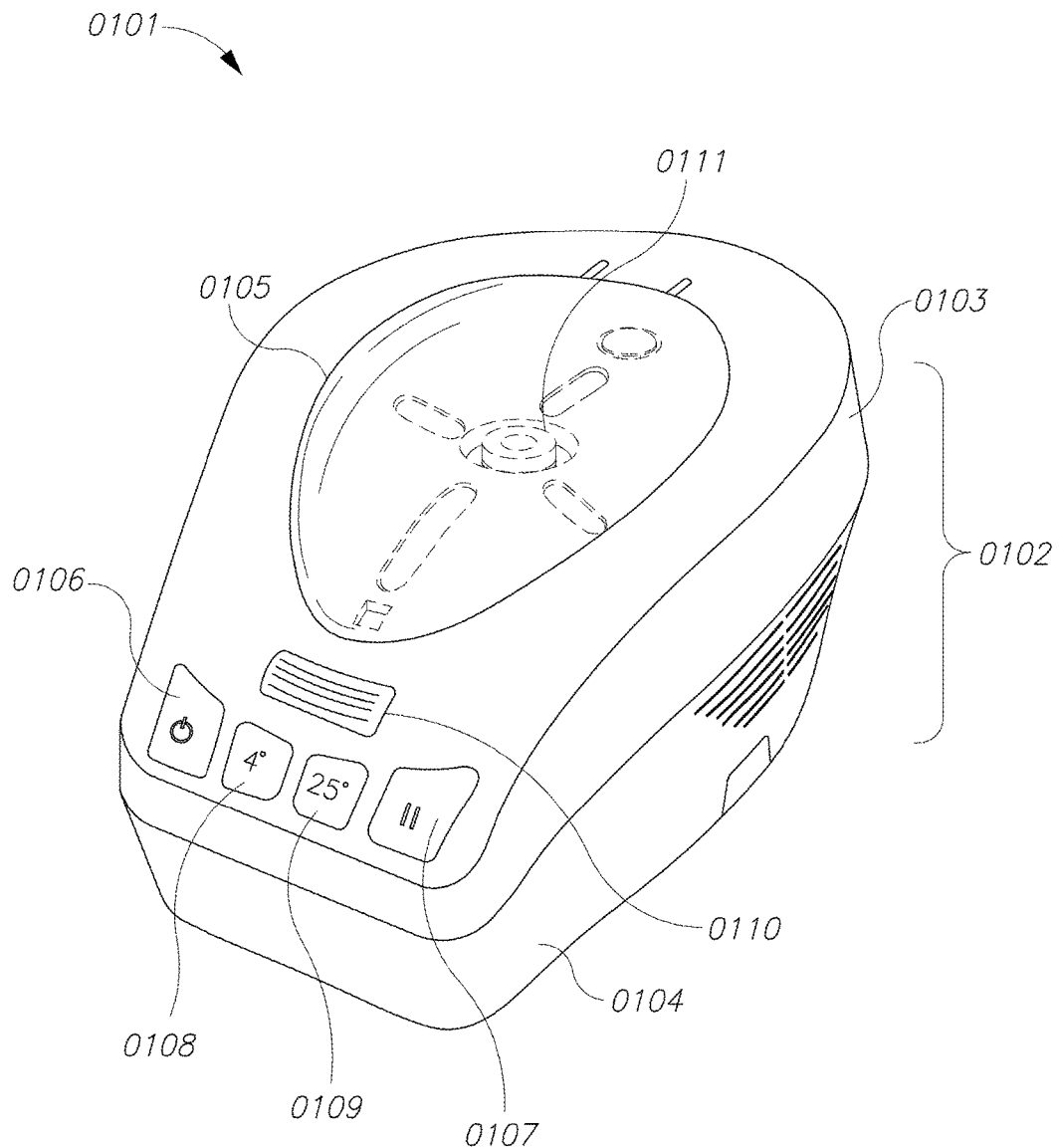
FIG. 1 illustrates a thawing system, according to an exemplary embodiment of the present disclosure.

FIG. 1 illustrates a thawing system 0101, according to an exemplary embodiment of the present disclosure. System can include a base 0102, comprising an upper assembly 0103 and a lower assembly 0104, and an optionally transparent lid 0105. Base can include one or more interfaces configured to receive operator input. For example, base can include one or more buttons, such as, an activation button 0106, a pause button 0107, a first target temperature button 0108, a second target temperature button 0109, a vial eject switch (not shown), and a lid release button 0110. The eject switch can aid extraction of one or more vials (not depicted) from the thawing chambers 0111, once an operator wishes to eject the vial from the system. In other embodiments, the base includes an interface (not depicted), optionally comprising a raise temperature button and a lower temperature button, configured to enable an operator to set a target temperature from a range of integral or non-integral (fractional) temperature values. The indentations surrounding the thawing chamber are decorative.

As explained below, lid 0105 may move to allow one or more vessels to be loaded into system. In some embodiments, system can be configured to receive a vial or container containing biological or chemical material.

Biological material can include material derived from a biological source. For example, biological material can include cells, peptides, nucleic acid, lipids, and carbohydrates. Various cells can be engineered to produce various natural and non-natural biological products. Cells can include eukaryotic and prokaryotic cells, including, for example, stem cells, bacterial cells, yeast cells, and various cell lines derived from biological sources.

System can be configured to receive one or more vials of various shapes and sizes. For example, system can be configured to receive an Eppendorf vial having a 1.6 ml capacity. Various other vials may be thawed using system.

Figure 2:
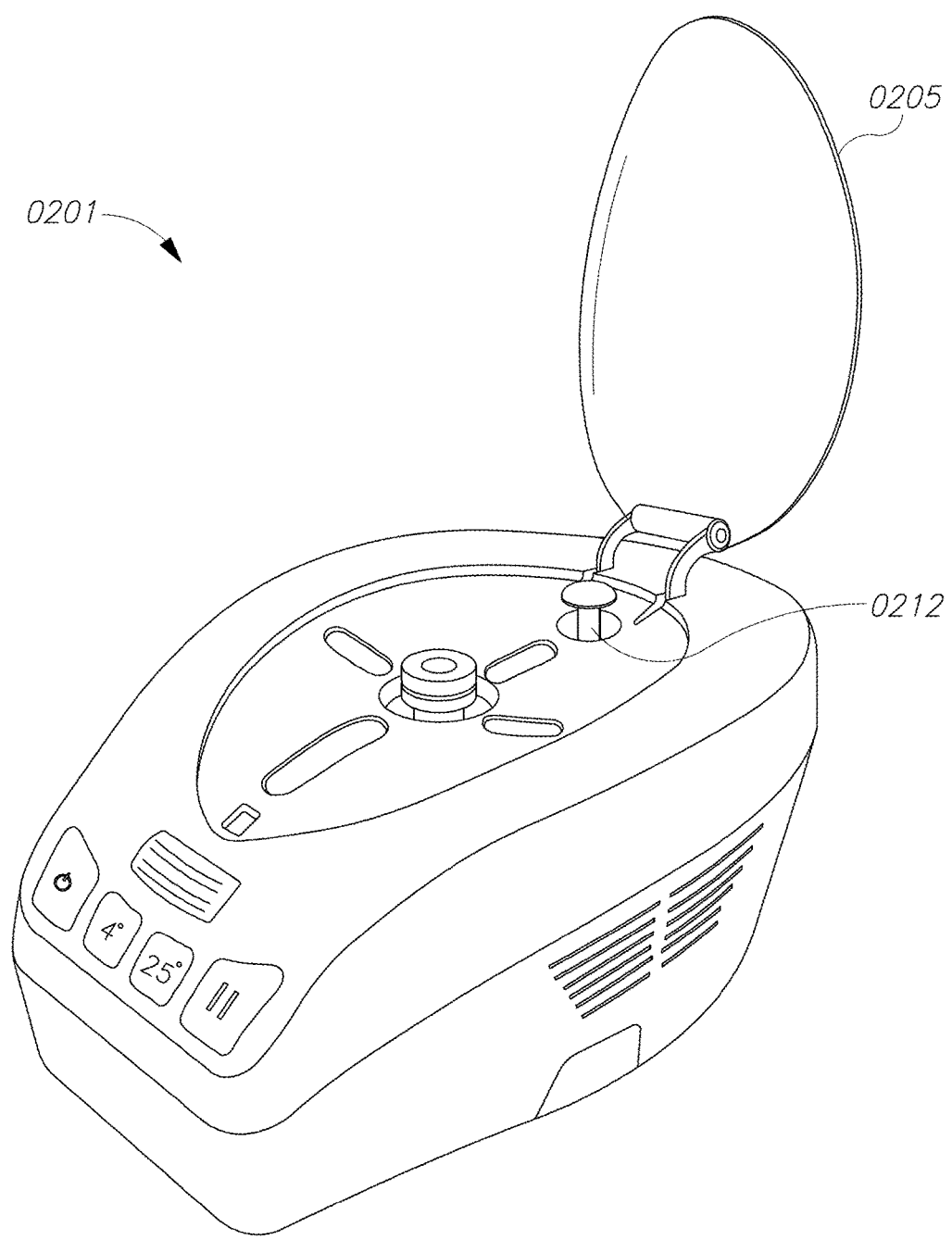
FIG. 2 illustrates a thawing system with an open lid, according to an exemplary embodiment of the present disclosure.

FIG. 2 illustrates a thawing system 0201 with an open lid 0205, showing a vial eject switch 0212 under the lid, according to an exemplary embodiment of the present disclosure. The lid 0205 may be comprised of a lightweight material, such as plastic. Various other materials are contemplated. Lid 0205 can maintain a generally closed environment and protect the user from moving parts. Lid 0205 may be moveably coupled to base to permit an operator to load one or more vials into system.

Figure 3:
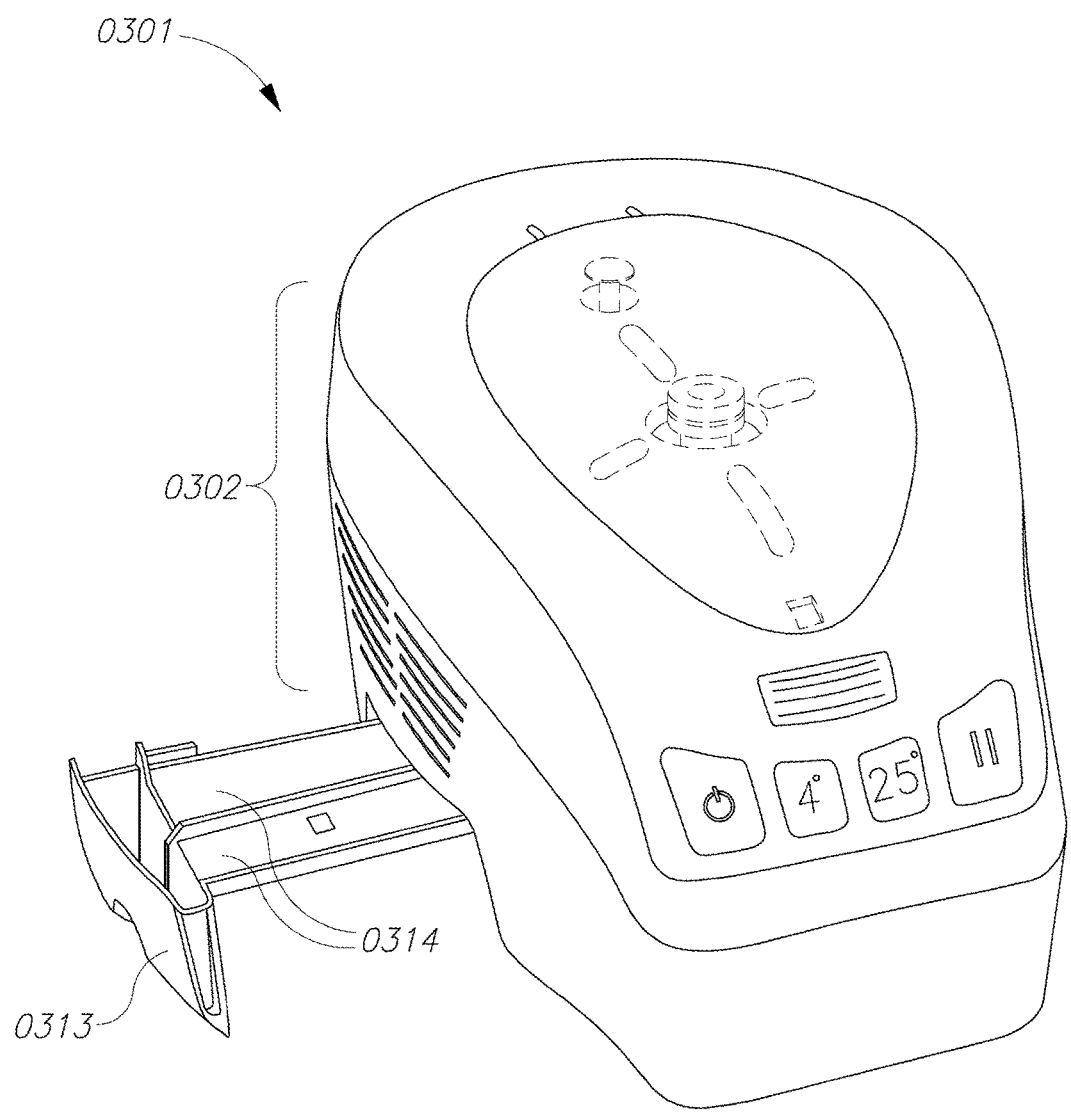
FIG. 3 illustrates a thawing system with an open water tray, according to an exemplary embodiment of the present disclosure.

FIG. 3 illustrates a thawing system 0301 with an open water collection drawer 0313, according to an exemplary embodiment of the present disclosure. Collection drawer can include a liquid collection tray 0314 configured to receive liquid collected by system. The drawer 0313 and/or liquid collection tray 0314 can collect water condensation or leakage, enabling clean work as needed for an aseptic environment, such as operation of a clean room or a surgery room. In some embodiments, drawer 0313 may be slidably coupled to base 0302 to allow drawer 0313 to be opened and emptied. In other embodiments, system can include a conduit to a sink or other receptacle (not depicted) to receive unwanted liquid collected by system.

Figure 4:
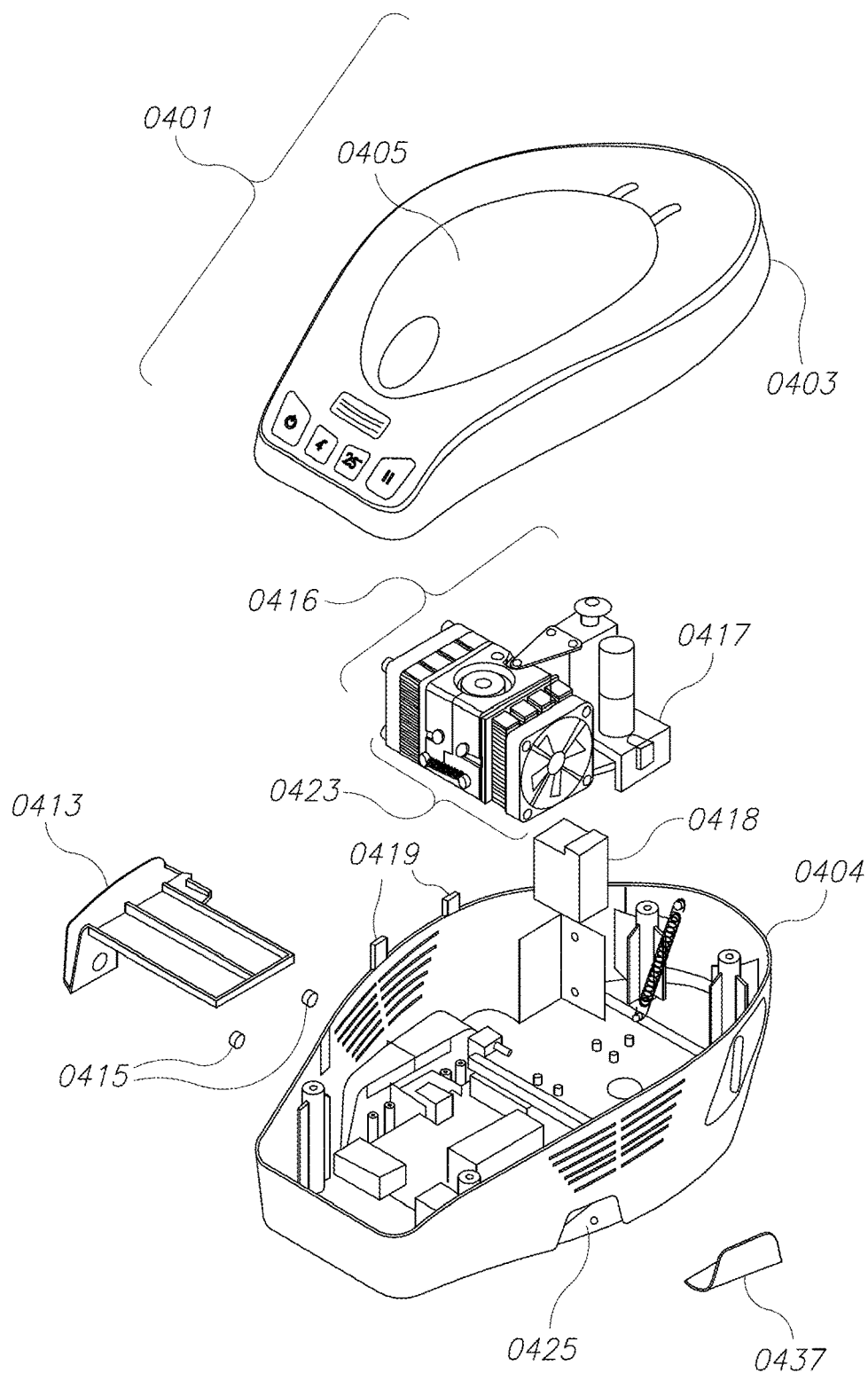
FIG. 4 illustrates an exploded view of a thawing system, according to an exemplary embodiment of the present disclosure.

FIG. 4 illustrates an exploded view of a thawing system 0401, according to an exemplary embodiment of the present disclosure. System is shown with lid 0405, upper assembly 0403, lower assembly 0404, collection drawer 0413, magnets 0415 or other devices for keeping the drawer 0413 closed, which may optionally be juxtaposed to metal plates 0419 on the lower assembly 0404, and heating device 0416. In certain embodiments, the magnets 0415 or other devices generate an alarm when the drawer 0413 is in the open position. Also depicted are a temperature control assembly 0423, and a port 0425 with cover 0437 for connection to an external computer or other device (not depicted) capable of programming the thawing system and/or transmitting data thereto or receiving data therefrom. In other embodiments, one or more of the described components may be not included or may be combined with other components, or additional components may be added to system.

The heating device 0416 may be configured to move, in some embodiments relative to the rest of lower assembly 0404. Various movement devices may be used with system. For example, the heating device 0416 may be equipped with a motor 0417 configured to rotate, oscillate, or otherwise move the heating device 0416 for purposes of mixing the contents of the vial or container during thawing. Such a motor could operate between 0-500 RPM, in some embodiments in a oscillating partial rotation.

Systems disclosed herein may also be equipped with a code or tag reader 0418 operably connected to the thawing chamber (not depicted) that can identify a serial number of one or more vials or containers (not depicted) disposed in the thawing chamber and store data associated with the one or more vials or containers, and optionally instruct the system based on information stored in the code or tag. Other functions based on code or tag information can include allowing activation, inhibiting use if the vial or container has passed an expiration date, inhibiting double thawing of the same vial or container, providing a program for warming the device, or providing calibration information. An alert could be generated based on such information. For example, an operator may be alerted that a vial or container is out of date, has previously been thawed, has remained within the device for too long, or has overheated. It is also contemplated that a code or tag may set one or more heating programs, including the heating time, the temporal profile of the energy input, and/or the target temperature, which may be the internal or external temperature of the vial or container. The code or tag may in some embodiments provide a control signal to a controller of the heating device, wherein the control signal is indicative of a target temperature to which the biological material is heated. This could allow running of different programs for different products set by the manufacture or various sample volumes. The code or tag may be, in various embodiments, any data capture device capable of being operably associated with a vial or container. Those skilled in the art will appreciate in light of the present disclosure that suitable codes and tags include but not are limited to a QR code, a UPC code, a barcode, an RFID (Radio Frequency Identification) tag, another type of identification tag, and a smart card. Various other types of devices configured to identify the contents of a vial or container are also contemplated.

In further embodiments, a code or tag stores information about the history of the vial or container with which it is associated. In some embodiments, the code or tag may store information about the custody chain and/or the cold chain of the vial or container. For example, if the vial or container has previously been thawed, the code or tag may transmit a signal to the thawing system that serves to inactivate a thawing program. In other embodiments, the code or tag may change color upon thawing, providing a visual warning to an operator.

Figure 5:
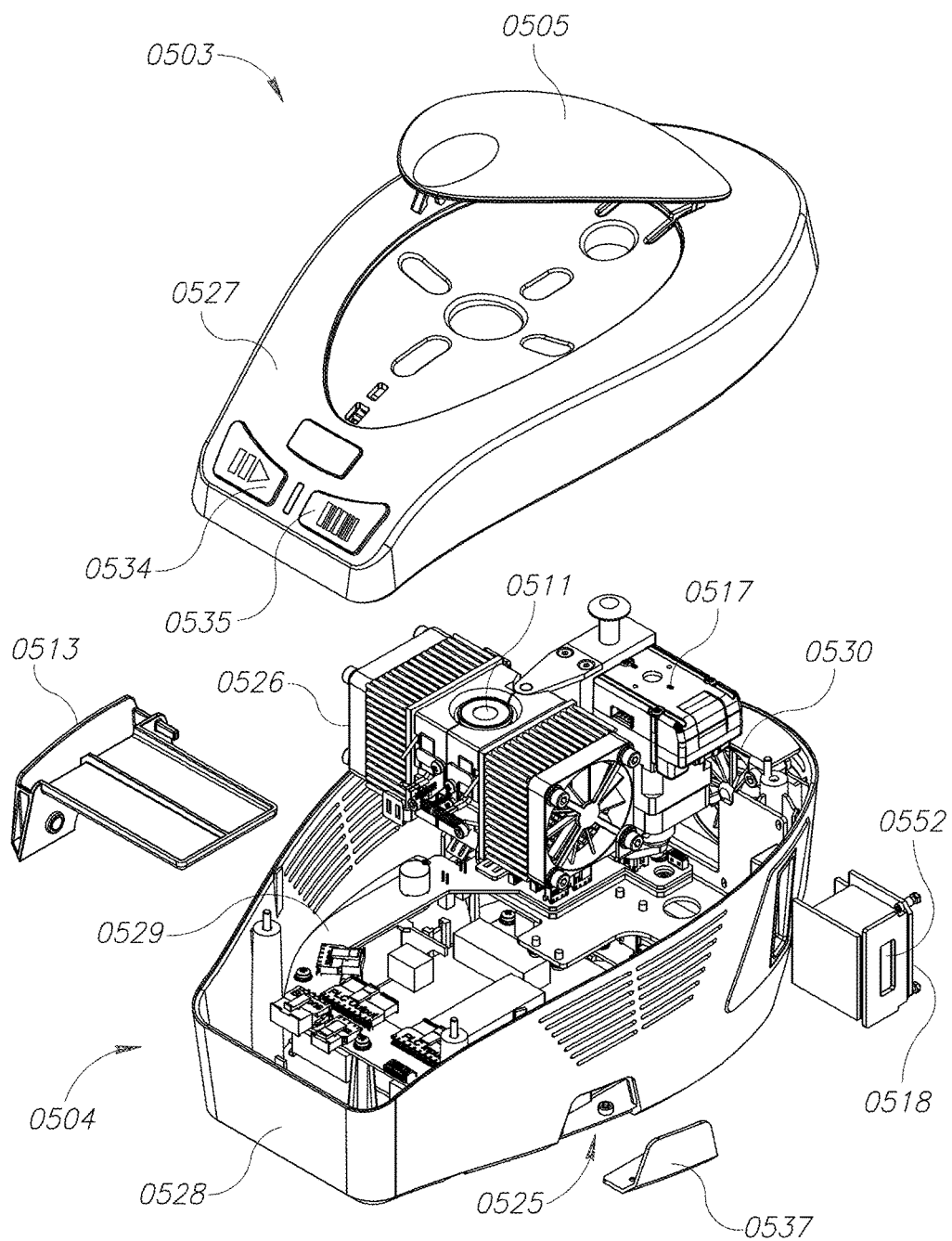
FIG. 5 illustrates an exploded view of a thawing system, according to an alternative exemplary embodiment of the present disclosure.

FIG. 5 illustrates an exploded view of a thawing system, according to an alternative exemplary embodiment of the present disclosure. System is shown with upper assembly 0503, including lid 0505, top shell 0527, a button for starting and stopping the thawing program 0534, and a button for reading the code or tag 0535. Lower assembly 0504 includes bottom shell 0528; main board 0529; thermal unit 0526; thawing chamber 0511 disposed within thermal unit 0526; stepper motor 0517, which is used to move thermal unit 0526; code or tag reader 0518; collection drawer 0513, and back fan 0530, which may be used for cooling thawing chamber 0511 at the end of the thawing process. Also depicted are a port 0525 for connection to an external computer or other device (not depicted) capable of programming the thawing system and/or transmitting data thereto or receiving data therefrom, and a cover of the port 0537. In some cases, the tag or code reader detects a vial or other container placed near the external window 0552 of the system. In other embodiments, one or more of the described components may be not included or may be combined with other components, or additional components may be added to system.

Figure 6:
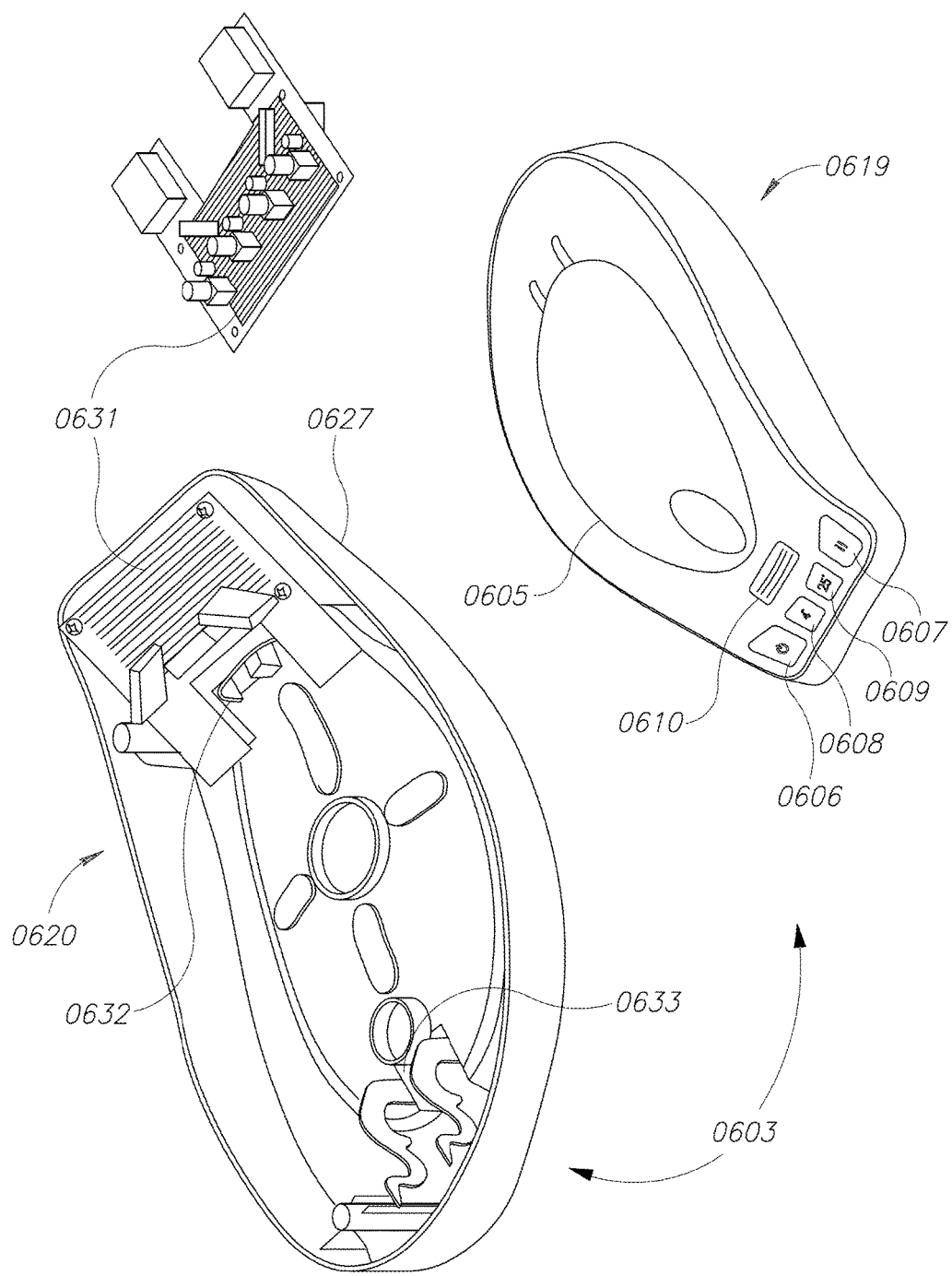
FIG. 6 illustrates top view and a bottom view of an upper section of a thawing system, according to an exemplary embodiment of the present disclosure.

FIG. 6 illustrates a top view 0619 and bottom view 0620 of an upper assembly 0603 of a thawing system, according to an exemplary embodiment of the present disclosure. Upper assembly can include top shell 0627, lid 0605 and one or more components—e.g. an activation button 0606, a pause button 0607, a first target temperature button 0608, a second target temperature button 0609, and a lid release button 0610—configured to receive user input. While several buttons are shown, lid 0605 can include other user interfaces (not depicted), such as, for example, a touch sensitive screen, a keyboard, or an interface to a remote device. Lid 0605 may also be moveably coupled to upper assembly using various mechanical linkages. The depicted connector assembly 0631 provides an interface between the buttons and the working parts of the system; and there may be a lid release assembly 0632, optionally disposed on the side proximal to the connector assembly 0631 and/or operably connected to the lid release button (not depicted); and/or there may be a hinge 0633, which may be disposed on the side distal from the connector assembly 0631. Upper assembly 0603 may also include one or more electrical components of system (not depicted). For example, a processor, memory, user interface, power source, or communication, module may be included in upper assembly. In other embodiments, one or more electrical components could be included in base or another part of system.

Figure 7:
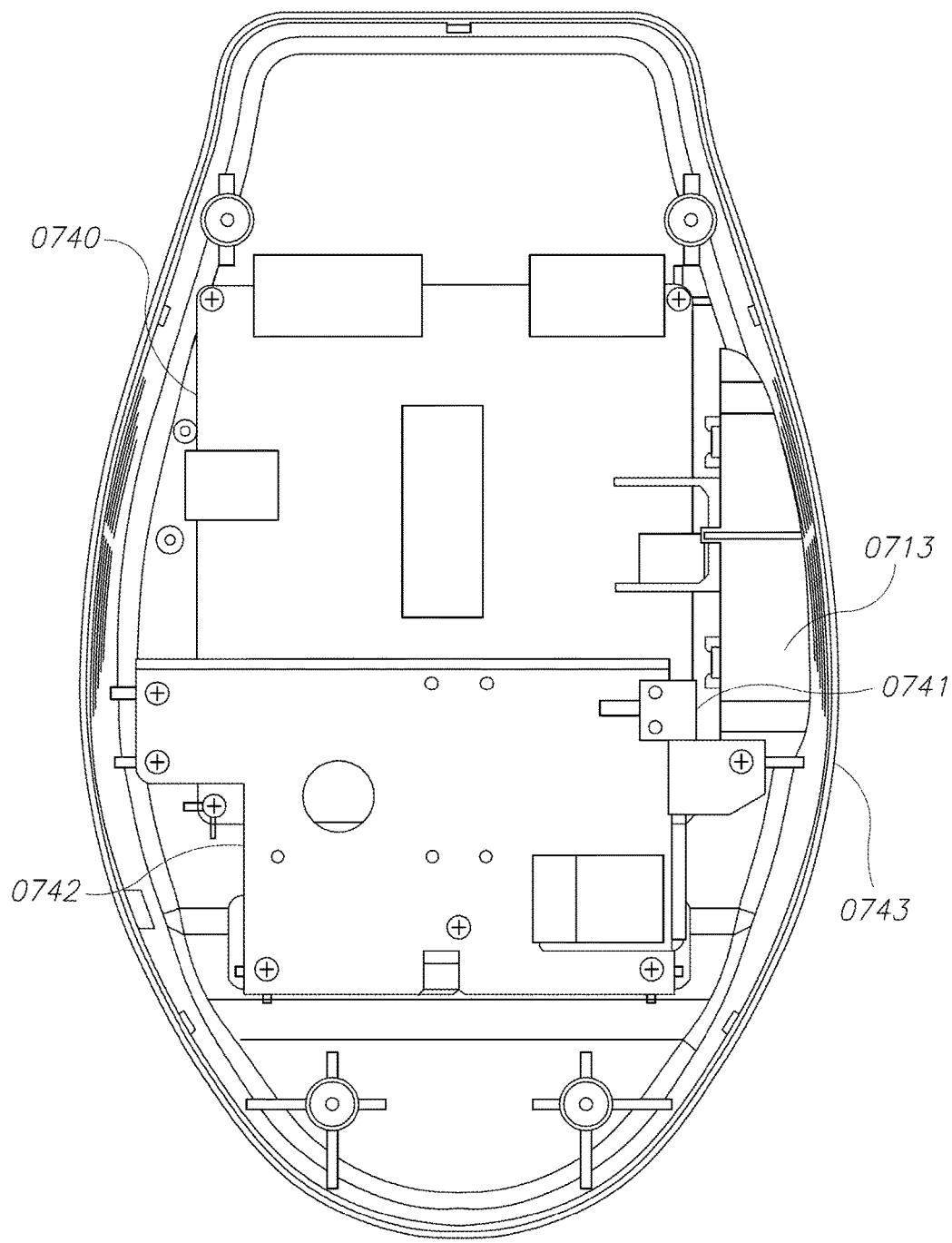
FIG. 7 illustrates a view of a base of a thawing system, according to an exemplary embodiment of the present disclosure.

FIG. 7 illustrates a top view of a lower assembly of a thawing system, according to an exemplary embodiment of the present disclosure. The lower assembly can include a controller board or processor 0740 (the function of which is described below), collection drawer 0713 with opto switch 0741, which may generate an alarm when the drawer 0413 is open, main bracket 0742, and bottom shell 0743, which in some embodiments provides protection for the internal components, and various other components of system. Power can be supplied from mains power (an alternating-current [AC]) or a direct current (DC) electric power supply. In some embodiments, for example where the system has a low voltage demand, it can be powered using a battery or portable power source. Lower assembly can also be moveably coupled to heating device (nor depicted), as described below.

Figure 8:
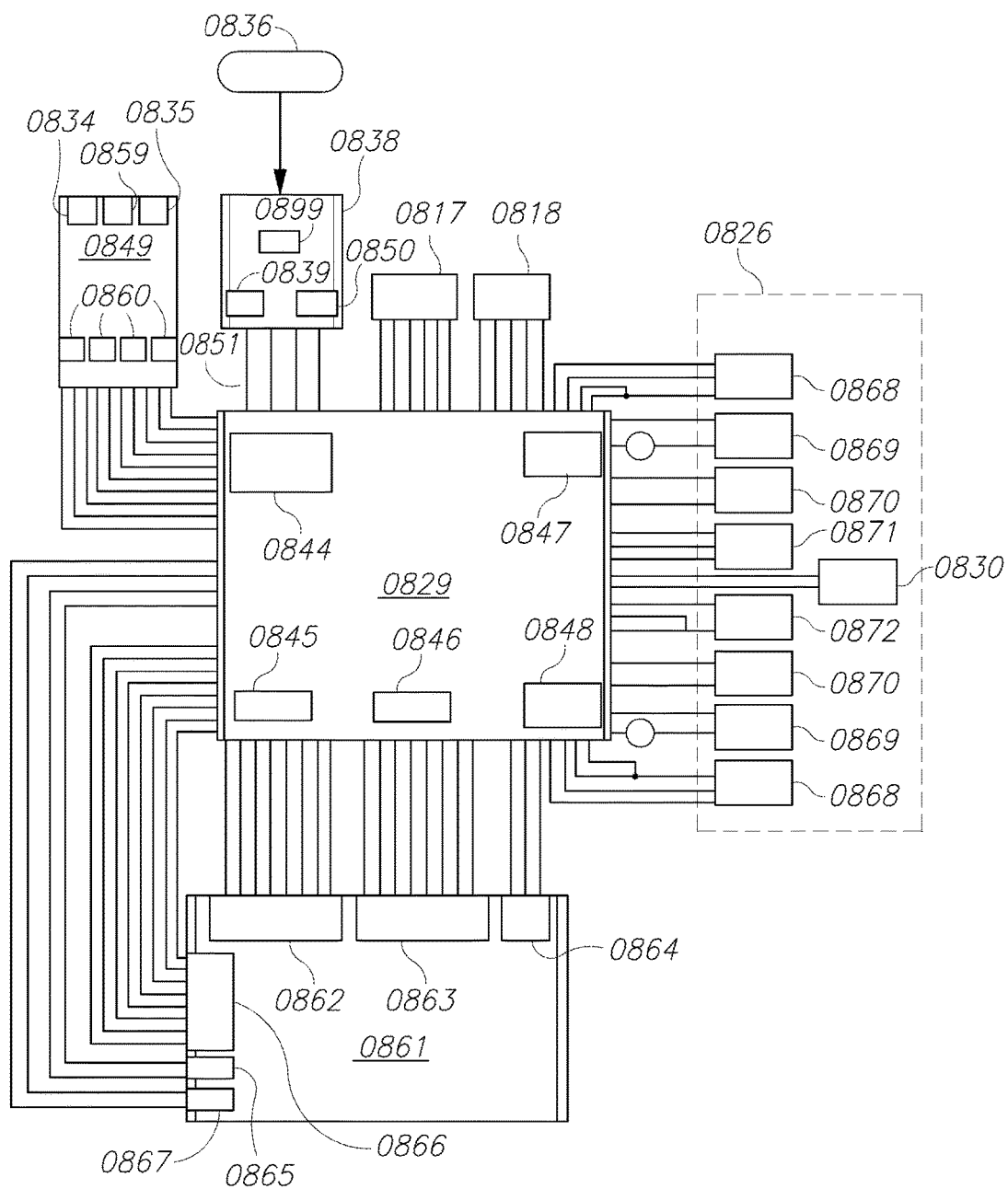
FIG. 8 illustrates a circuit diagram of a thawing system, according to an exemplary embodiment of the present disclosure.

FIG. 8 illustrates a circuit diagram of a thawing system, according to an exemplary embodiment of the present disclosure, showing the external power supply to the system 0836, which provides a 13-Volt direct current. The power enters the system's power card 0838, containing indicator LED 0839, switch 0849, fuse 0850 and connectors 0851. The power then enters the main board 0829, which diverts it from there to the system's components. The main board 0829 contains a voltage converter 0844, which may be a 5-volt power supply, tray optic sensor 0845, buzzer 0846, H-bridge 1 0847, and H-bridge 2 0848. Main board is operably connected to: buttons board 0849, which contains a button for starting and stopping the thawing program 0834, and a button for reading the code or tag 0835, door sensor 0859, and LED's 0860; motor 0817; code or tag reader 0818; thermal unit 0826, which includes 2 block temperature sensors 0868, two thermoelectric coolers 0869, two small fans 0870, a vial optic sensor 0871, and a vial temperature sensor 0872; a back fan 0830; and a programmable logic controller 0861, configured for digital output 0862, digital input 0863, RS232 communication 0864, RS485 communication 0865, analog I/O 0866, and a power line 0867. The voltage converter 0844 converts the 13 Volt current to 5 Volts. This voltage is used on the buttons board 0849 for the LEDs and the optic sensor and on the code or tag reader 0818.

Figure 9:
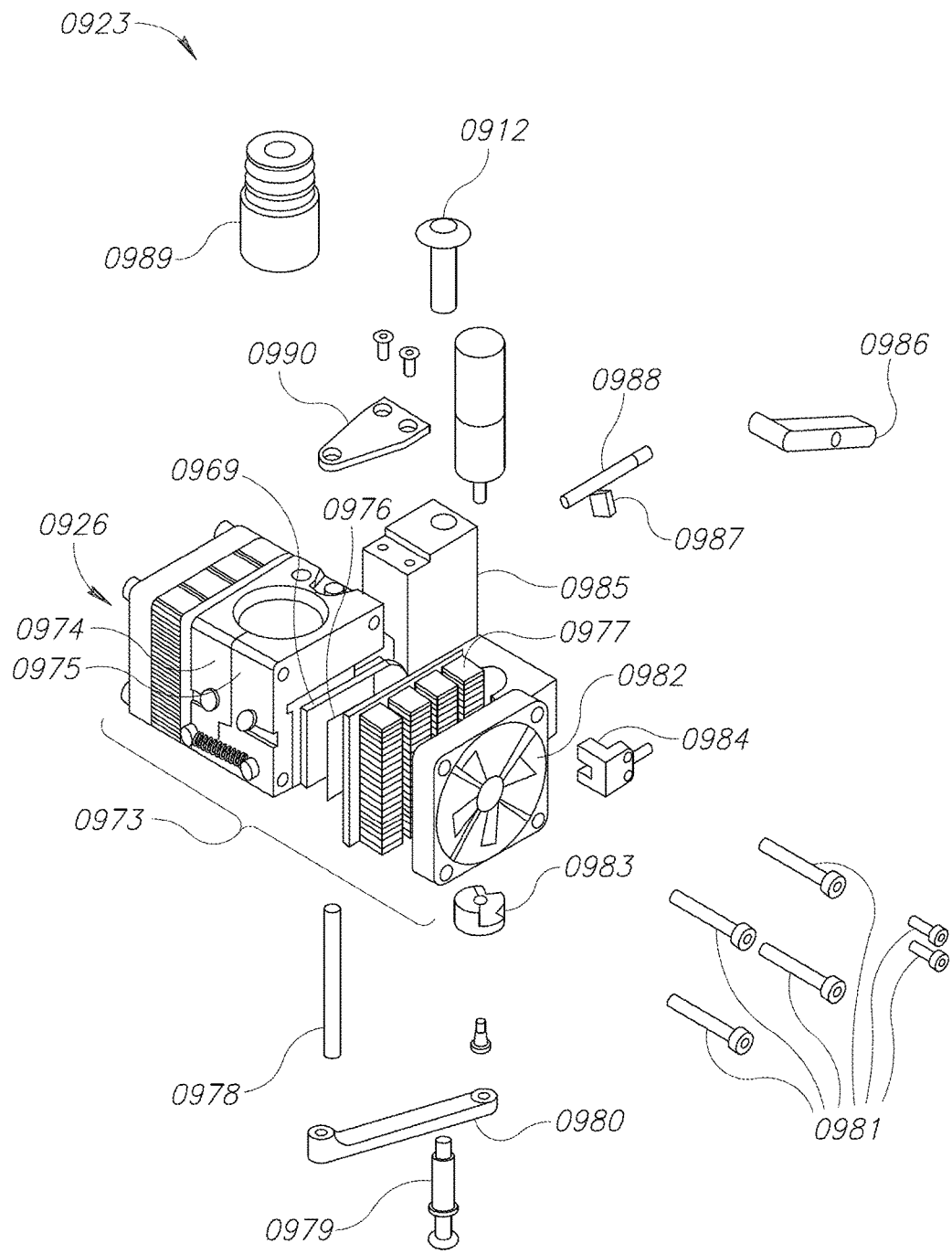
FIG. 9 illustrates a view of a heating device of a thawing system, according to an exemplary embodiment of the present disclosure.

FIG. 9 illustrates a partially exploded view of a heating device 0923 of a thawing system (not depicted), according to an exemplary embodiment of the present disclosure. Heating device 0923 can be rotatably or otherwise movably coupled to base (not depicted) or other part of system. Alternatively, (not depicted), the system may be configured to controllably move a vial or other container containing a biological or a chemical material, relative to heating device 923. Main body 0973 contains left heating block 0974 and right heating block 0975, adjacent to, on each side moving outward, thermoelectric cooler 0969, carbon foil 0976, heat sink 0977, and fan 0982. Also depicted are main hinge 0978, vial release rod 0979, main arm 0980, bolts 0981, motor plug 0983, motor position plug opto-switch 0984, assembly base 0985, vial release lever 0986, vial release micro switch 0987, vial release shaft 0988, vial release button 0912, vial 0989, and top bracket 0990.

Figure 10:
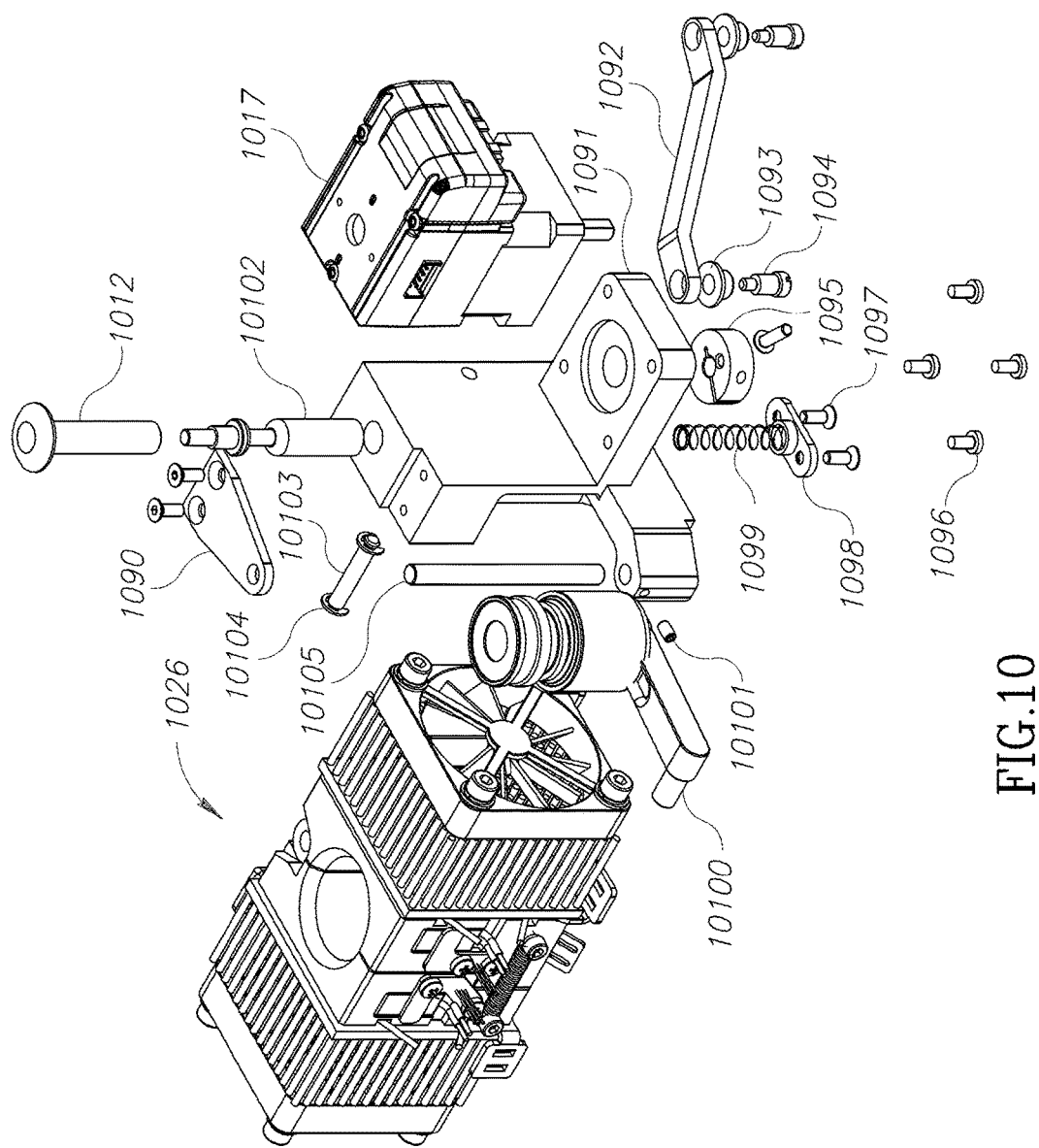
FIG. 10 illustrates a view of a heating device of a thawing system, according to an exemplary embodiment of the present disclosure.

FIG. 10 illustrates a partially exploded perspective view of a heating device of a thawing system, according to an exemplary embodiment of the present disclosure. Depicted are thermal unit 1026, stepper motor 1017, which serves in some embodiments to move thermal unit in an oscillating, partially rotating motion, base 1091, arm 1092, sliding bearing 1093, shoulder screw 1094, excenter 1095, pan head screws 1096, spring cover screws 1097, which may be socket countersunk head screws, spring cover 1098, compress spring 1099, button leg 10100, socket set screw 10101, button shaft 10102, vial/container release button 1012, top bracket 1090, leg pin 10103, lock washer 10104, and lever pin 10105.

Figure 11:
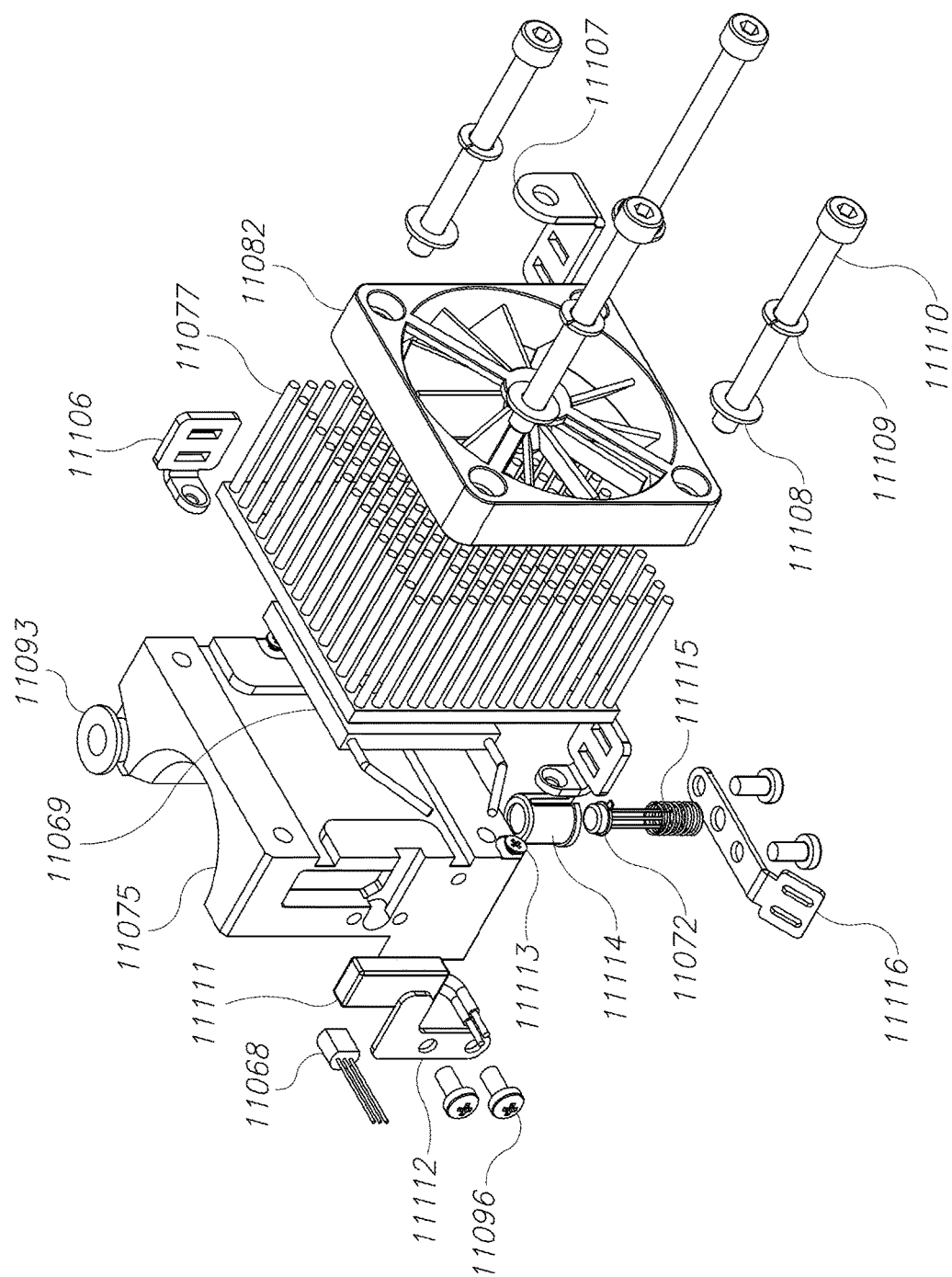
FIG. 11 illustrates an exploded view of a right-side of a heating device of a thawing system, according to an exemplary embodiment of the present disclosure.

FIG. 11 illustrates an exploded perspective view of a right-side of a thermal unit of a thawing system, according to an exemplary embodiment of the present disclosure, including right heating block 11075, thermoelectric cooler 11069, heat sink 11077, sliding bearing 11093, cable holder 11106, fan 11082, longer cable holder 11107, flat washer 11108, spring washer 11109, socket cap screw 11110, thermal switch 11111, temperature sensor 11068, right closing plate 11112, pan head screw 11096, countersunk flat head screw 11113, thermal sensor housing 11114, vial temperature sensor 11072, compress spring 11115, and bottom closing plate 11116.

Figure 12:
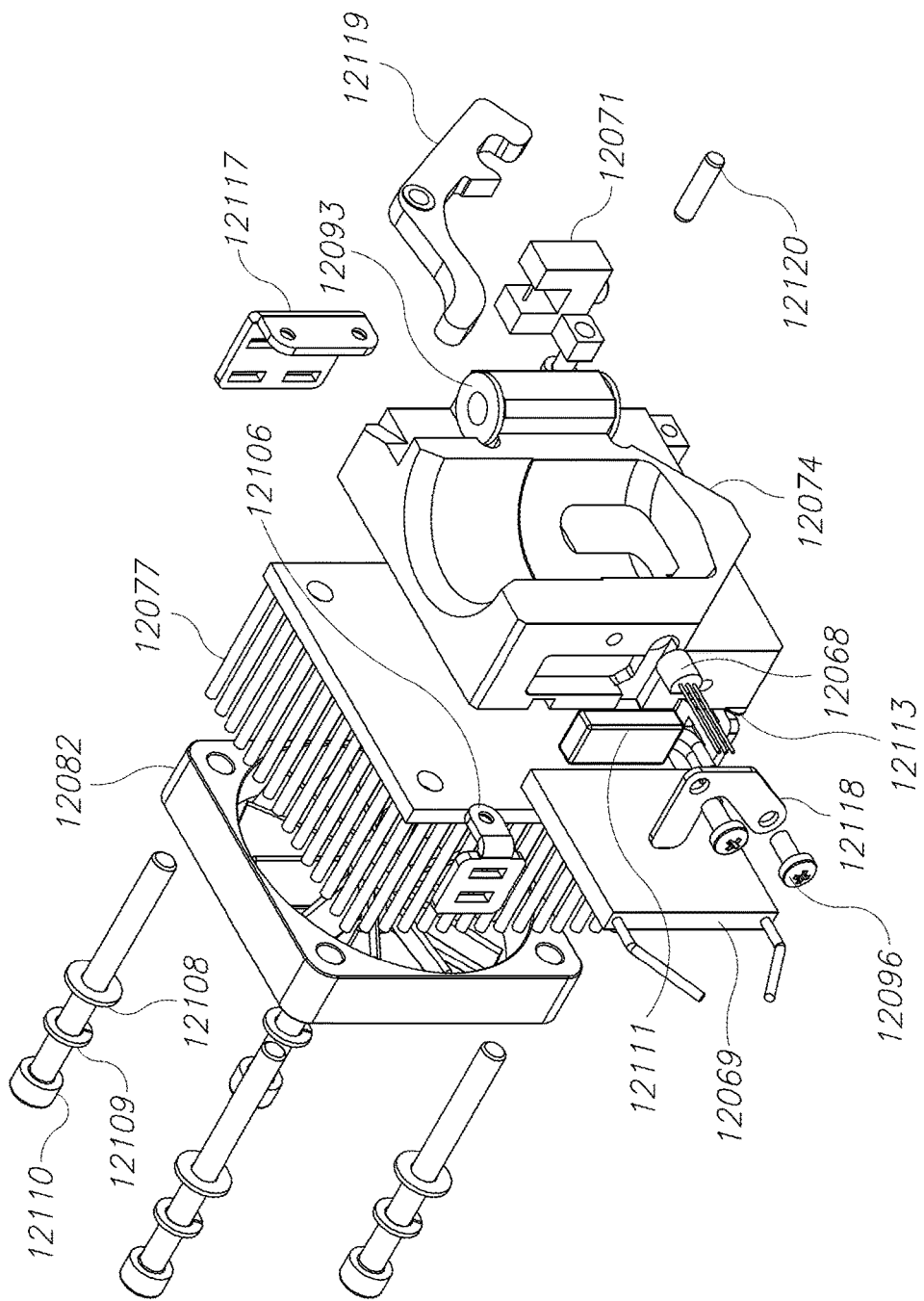
FIG. 12 illustrates an exploded view of a left side of heating device of a thawing system, according to an exemplary embodiment of the present disclosure.

FIG. 12 illustrates an exploded view of a left side of thermal unit of a thawing system, according to an exemplary embodiment of the present disclosure, including left heating block 12074, thermoelectric cooler 12069, heat sink 12077, sliding bearing 12093, cable holder 12106, fan 12082, double cable holder 12117, flat washer 12108, spring washer 12109, socket cap screw 12110, thermal switch 12111, temperature sensor 12068, left closing plate 12118, pan head screw 12096, countersunk flat head screw 12113, lever 12119, parallel pin 12120, and vial optic sensor 12071.

Figure 13:
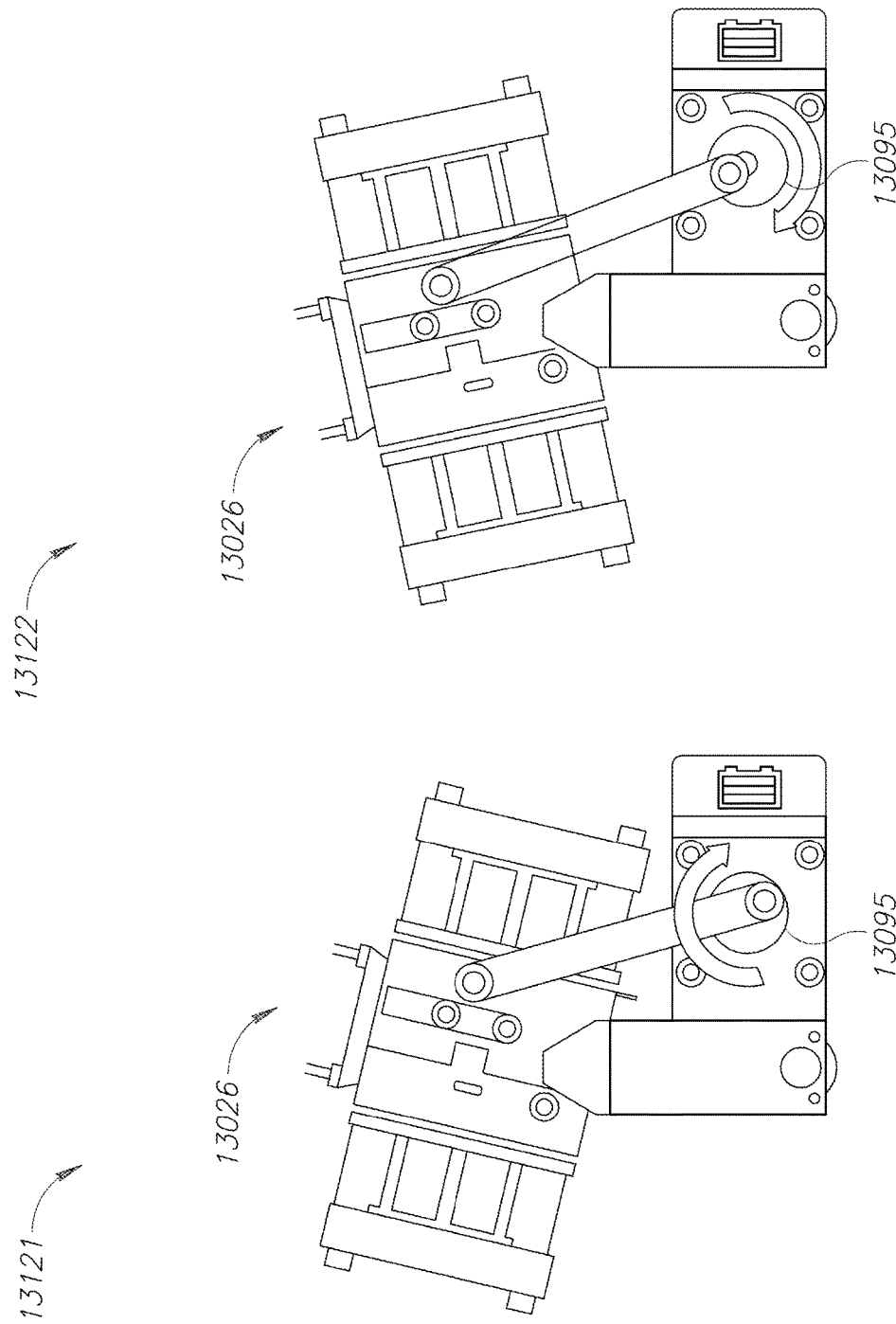
FIG. 13 illustrates a view of motion of a heating device, relative to a base of a thawing system, according to an exemplary embodiment of the present disclosure.

FIG. 13 illustrates a view of motion of a heating device or thermal unit 13026, including excenter 13095, relative to a base of a thawing system, according to an exemplary embodiment of the present disclosure, shown in the extreme right-tilted position 13121 and in the extreme left-tilted position 13122. In the depicted embodiment, the total rotation angle (from one end to the other) of the thermal unit is 26 degrees of rotation (on a 360 degree scale).

As mentioned, a thermal unit may be configured to move, in some embodiments relative to the base of the system. Various movement devices may be used with system. For example, the heating device may be equipped with one or more motors configured to rotate, oscillate, or otherwise move the heating device. Such a motor could operate at a speed between 0-500 RPM. In certain embodiments, the heating device is partially rotated in a oscillating motion, in preferred embodiments with a total rotation range (the angular range between the 2 extreme positions of the device) between 10-180° (10-180 degrees of rotation), between 20-160°, between 20-150°, between 30-140°, between 30-120°, between 35-110°, between 35-100°, between 35-90°, between 35-80°, between 35-70°, between 40-70°, between 35-60°, between 40-60°, between 45-65°, between 10-40°, between 10-35°, between 15-40°, between 15-35°, between 17-36°, between 18-36°, between 18-35°, between 18-34°, between 19-33°, between 20-32°, between 21-31°, between 22-30°, between 23-29°, between 24-28°, between 25-27°, about 26°, or 26°. Alternatively or in addition, the rotation speed is between 1-500 between 21-31°, between 22-32°, RPM, between 10-400 RPM, between 20-400 RPM, between 30-400 RPM, between 40-400 RPM, between 50-350 RPM, between 50-350 RPM, between 50-300 RPM, between 60-350 RPM, between 60-300 RPM, between 80-300 RPM, between 100-300 RPM, between 100-250 RPM, or between 100-200 RPM. Various other motors could be changed to provide various speeds or speed profiles. For example, the motor could be configured to operate at constant speed or variable speed.

Figure 14:
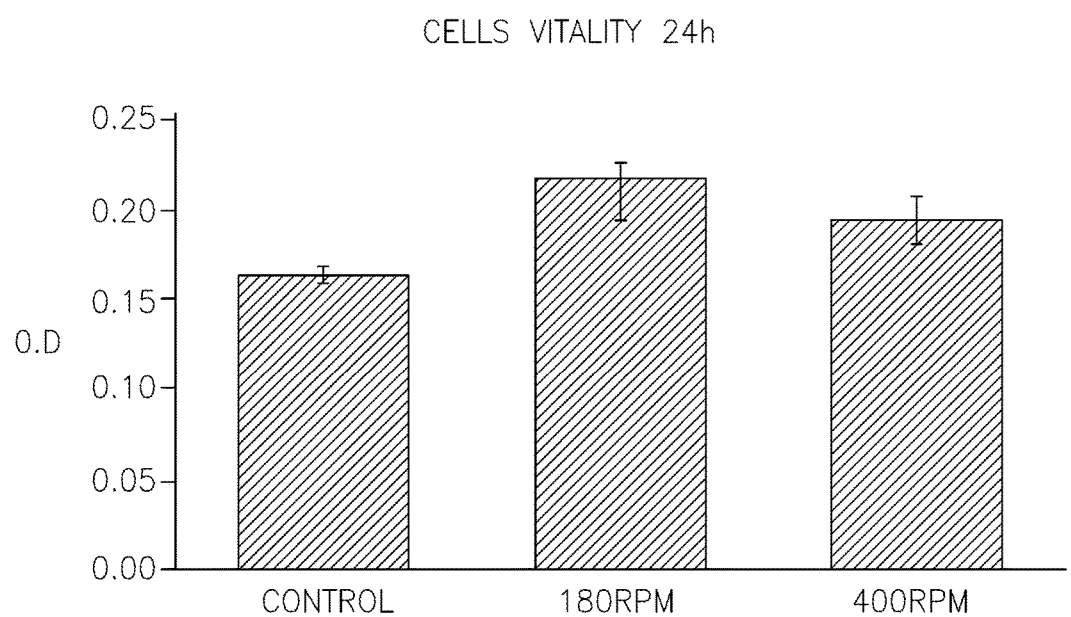
FIG. 14 illustrates a chart showing cellular vitality from use of a thawing device, according to an exemplary embodiment of the present disclosure.

FIG. 14 illustrates a chart showing cellular vitality from use of a thawing device, according to an exemplary embodiment of the present disclosure. Placenta-derived adherent stromal cells (PLX-PAD) were thawed in a thawing device following long-term cryopreservation in liquid nitrogen (−195° C.). The data demonstrates higher viability when rotating the thawing device at, for example, either 180 or 400 RPM agitation rates. Other cell types, storage conditions, heating temperatures, and agitation rates may also provide improved cellular vitality compared with typical use of water bath by an average operator. The system thus reduces operator error and variability in thawing multiple samples, enhancing the reproducibility of thawing for batch processing.

Various heating mechanisms can be used to transmit heat to a material in a vial or a container, e.g. a biological material. For example, electro-resistive heating, microwave, ultrasound, and other heating modalities can be used. In some embodiments, the system can include a water heater configured to operate at one or more specific temperatures.

For example, the heating device can include a heating block as described hereinabove, configured to receive one or more vials of different size and shape. Heating device can have one or more sensors configured to detect the temperature of the vial or container. For example, heating device can include one or two heat-sensing probes. Multiple heating probes can be used to reduce or eliminate over-heating of biological or chemical material.

In still other embodiments is provided a system for heating a biological material in a vessel, comprising:
- a body having a base;
- a receiver disposed within the body, the receiver being configured for receiving a vessel; and
- a heating device movably coupled with the base and configured to transmit thermal energy to a vessel present in the receiver.

In other embodiments, an IR thermometer can be added to the system to measure a temperature associated with the outside wall of the vial or container. A known correlation may be used to determine or approximate the temperature of a solution or biological material contained within the vial or container, which was originally frozen and is being heated, and thus thawed or in the process of being thawed, while being measured. Various other types of thermometers could be used with the system.

The heating device can also include one or more cooling devices to assist in temperature regulation. For example, heating device could include one or two fans located on opposite sides of heating device, as described above.

In some embodiments, the motor can have one reference point for each round. The reference point can be set to HOME. The controller can calculate the rotation speed of the motor by the time that passes between the reference point transitions. The speed control can be essentially recursion speeds of previous rounds. For example, the next round velocity can be half the speed of the previous round, a quarter of the speed of rotation before, and so on. That is, as the speed gets closer to the target, the amendments made to it can get smaller.

Operation of Thawing System

System can be configured to operate with various biological or chemical materials. For example, system can include a first target temperature of 4° C. and a second target temperature of 25° C.

The thawing procedure of system can be based on automatically shaking the vial at a generally constant temperature. Constant temperature may be achieved, for example, using a temperature-controlled chamber or heating block, which can for example be made of aluminum, where the chamber or block is maintained at constant temperature. Heating can occur for a predetermined time period. In other embodiments, the device temperature and shaking speed, as well as the thawing time, can be adjusted in order to fit the thawing conditions for different sample volumes and solutions.

In some embodiments, system can include a processor or controller. The controller can be configured to receive information from one or more sources. For example, the controller can be configured to operate with one or more heat sensors, a time counter, a speed monitor and a code or tag reader. Using the controller, system can be programmed to follow various thawing protocols. These protocols can be set by an operator. One exemplary embodiment is outlined below, and other protocols are also contemplated.

Initially, a thawing cycle may active only after the heating device has reached a predetermined temperature. This may reduce the effect of room and/or previous device temperature on the thawing procedure.

During a thawing protocol, a controller may be configured to control a shaking speed of a vial or container disposed within the system. The controller may also adjust vial movement speed when the operation exceeds the maximum thawing speed boundary.

The controller may also control a temperature of the heating device during a run. For example, the controller may reduce the heating device temperature when the operation exceeds the maximum thawing temperature boundary. System can include a sensor, for example an IR thermometer, specifically configured to monitor conditions within the vial.

System can be equipped with two temperature sensors localized in the two sides of heating device or thawing chamber. Further, the controller can activate two heating elements separately based on the temperature measured by each sensor. In certain embodiments, the two heating elements each heat one of two (or more) separate heating blocks, and the thawing chamber is disposed between the heating blocks. In further embodiments, each heating element may itself be sufficient to bring the sample to the desired temperature, for example if the other heating element fails to operate as required. If the measured temperature is lower than the target temperature (e.g., 38° C.), the heating force can increase. If the target is approaching the target temperature, the heating force or level of added heat can decrease. When one of the temperature probes reaches the target temperature, the heating may be stopped in both heating blocks. If one of the sensors indicates a temperature higher than 39° C., the device can start cooling until the higher temperature of the two measured falls below 39° C.

When system operates in the range of 38° C. to 39° C. degrees, there may be no heating or cooling, e.g. in order to save electricity.

System may be configured to produce a warning when the operation exceeds the maximum thawing temperature boundary or the maximum thawing speed boundary. A thawing cycle may be stopped based on a temperature associated with vial or container, the contents thereof (e.g. a biological material), heating device, or other metric. For example, if a temperature sensor is present, the run may be terminated based on the measured or estimated vial temperature. Calculation of the sample contents of the vial or container may utilize a known correlation between external and internal temperature for a given container or container/sample combination. The run may also be terminated based on a software algorithm that calculates either the exact point of the solid to liquid phase. In other embodiments, a cycle time (i.e. a predetermined heating profile) may be used to reach a more precise thawing temperature. Those skilled in the art will appreciate in light of the present disclosure that temperature sensors suitable for the system include IR sensors thermocouple sensors, thermistors and thermistor type sensors, LM35 sensors, LM36 sensors, platinum resistance thermometers, and other sensors and thermometers capable of measuring the outer wall temperature of a vial or similar container.

System may also be configured to keep the vial or container at a controlled temperature at various stages throughout a run. For example, temperature may be maintained at higher or lower than the initial thawing temperature at the end of a thawing procedure until the vial or container is extracted for use, which may be referred to as "standby mode". In still other embodiments, the system has a separate chamber for maintaining one or more vials that have already been thawed at constant temperature, while additional vials are being thawed.

System may be further configured to activate the thawing cycle upon detecting a unique structure of a code or tag. System could, for example, compare the detected code against the device database in order to prevent a repeat processing of the vial or container. Other actions may be based on a variety of identifier information, such as, for example, information obtained using an ID tag reader.

In some embodiments, a display may be included. For example, a Human-Machine Interface (HMI) display can be added in order to display the thawing process parameters or error indications. System could be configured to store information on multiple runs (e.g. up to 100 runs) including, for example, vial ID number, duration, date and time of thawing, and error indications.

As indicated above, system can be configured to receive, store, and transmit various data associated with the contents of the vial or container, e.g. a biological material. For example, data can be extracted and imported from system by a network connection. System can also be programmed to extract a report summarizing the thawing process data.

In some embodiments, system can be operated using one or any number of the following steps:
1. Open the device by switching the rear electrical switch to the on mode;
2. Press on the activation switch or read the code or tag;
3. Wait for the chamber pre-warm to 37° C., as indicated by a signal;
4. Press on the lid release button and open the lid;
5. Assure that the thawing chamber is centered;
6. Insert a vial into the chamber by pressing the vial down;
7. Close the lid;
8. Press on the "25° C." button or start (activating an automatic program set by identifying the code or tag);
9. The thawing chamber will start to shake in a predetermined speed (RPM) for the predetermined thawing time;
10. At the end of the thawing time, the system will generate an alert and immediately will switch to standby mode, to preserve a constant temperature;
11. When the sample is desired to be removed, to open the lid, press the lid release button;
12. Push the vial extraction button down until the vial can be grabbed and extract the vial;
13. Close the lid; and
14. Repeat steps 4 to 12 for an additional vial(s) to be thawed.

By way of example, FIG. 8 illustrates a chart showing cellular vitality from use of a thawing device, according to an exemplary embodiment of the present disclosure. Using system can lead to better post-thaw cell vitality compared to a water bath. Using different thawing speeds (RPM) may have an effect on post-thaw vitality of the cells. The depicted data were generated using 6 ml Crystal vials (Aseptic Technologies) filled with 5.5 ml cell suspension, with 3 vials per group.

Other embodiments of the disclosure will be apparent to those skilled in the art from consideration of the specification and practice of the present disclosure. It is intended that the specification and examples be considered as exemplary only.

What is claimed is:

1. A system for thawing a frozen biological material in a vessel, the system comprising:
    a lower base;
    a temperature control assembly comprising a thawing chamber enclosing the vessel, the temperature control assembly including:
        a first heating block and a second heating block, end faces of the first and second heating blocks at least partially abutting one another, the thawing chamber being defined by recesses in the end faces of the first and second heating blocks, each of the heating blocks configured to cooperate with one another to heat the thawing chamber to a target temperature;
        a first temperature sensor operably associated with the first heating block and configured to read a temperature of the first heating block; and
        a second temperature sensor operably associated with the second heating block and configured to read a temperature of the second heating block,
    wherein the temperature control assembly is configured to transmit energy to the vessel;
    a motor coupled to the temperature control assembly and configured to move the temperature control assembly in an oscillating, partially rotating motion relative to the lower base; and
    a processor configured to:
        (a) receive an input associated with the target temperature; and
        (b) transmit a signal to cause the motor to controllably move the temperature control assembly and the vessel together relative to the lower base for a time period, resulting in generally uniform heat dispersion during thawing of the frozen biological material,
    wherein the time period is determined based on at least the target temperature and a content volume of the biological material, and
    wherein the frozen biological material comprises viable cells.

2. The system of claim 1, wherein the vessel is a vial or tube.

3. The system of claim 1, wherein the viable cells comprise placenta-derived stromal cells.

4. The system of claim 1, wherein the frozen biological material is cryopreserved.

5. The system of claim 1, wherein the processor is configured to transmit a signal to controllably rotate or oscillate the temperature control assembly relative to the base.

6. The system of claim 1, wherein the processor is configured to transmit a signal to controllably rotate the temperature control assembly at a speed between 1-500 RPM relative to the base.

7. The system of claim 1, wherein the processor is configured to transmit a signal to controllably rotate the temperature control assembly at a speed between 180-400 RPM relative to the base.

8. The system of claim 1, wherein the processor is configured to transmit a signal to controllably rotate the temperature control assembly with a total rotation range between 10-180 degrees.

9. The system of claim 1, wherein the processor is configured to transmit a signal to controllably rotate the temperature control assembly relative to the base at a variable speed.

10. The system of claim 1, wherein the system results in improved cellular vitality compared to an otherwise similar system without moving the temperature control assembly.

11. The system of claim 1, wherein when either of the first or second temperature sensor detects that the temperature of the thawing chamber is higher than the target temperature, both of the heating blocks stop heating the thawing chamber.

12. The system of claim 1, wherein the temperature control assembly further comprises a first cooling device operably associated with the first heating block and a second cooling device operably associated with the second heating block, wherein when the first or second temperature sensor detects that the temperature of the thawing chamber is higher than the target temperature, the first or second cooling device cools the thawing chamber.

13. The system of claim 12, wherein the first or second cooling device comprises a thermoelectric cooler.

14. The system of claim 12, wherein the first or second cooling device comprises a fan.

15. The system of claim 1, wherein the system is configured to keep the biological material at a constant temperature after thawing.

16. The system of claim 1, further comprising a code or tag reader configured to identify a code or tag associated with the vessel.

17. The system of claim 16, wherein said vessel further comprises a code or tag that is readable by said code or tag reader.

18. The system of claim 1, further comprising a memory configured to store data associated with at least one of a temperature of the first heating block, a temperature of the second heating block, a temperature of the vessel, a temperature of the biological material, a speed of movement of the temperature control assembly, and the time period.

19. The system of claim 18, further comprising a network connection configured to transmit said data to a network.

20. The system of claim 1, wherein the first heating block and the second heating block each include separate respective heating means.

21. The system of claim 1, configured to maintain the vessel at a temperature below an initial thawing temperature at the end of a thawing procedure in a standby mode until the vessel is extracted from the system for use.

22. The system of claim 1, further comprising a vessel ejection system including an eject switch which, when depressed, ejects the vessel from the thawing chamber.

23. The system of claim 14, wherein the temperature control assembly includes two fans located on opposite sides of the temperature control assembly.

24. The system of claim 16, wherein the code or tag reader provides the system with a program for the temperature control assembly based on information stored in the code or tag associated with the vessel.

25. The system of claim 1, further comprising a vessel temperature sensor configured to read a temperature of the vessel when the vessel is disposed in the thawing chamber.

26. A method of thawing a frozen biological material in a vessel, comprising:
(i) providing the system of claim 1,
(ii) placing the vessel in the thawing chamber,
(iii) applying heat to the frozen biological material via the temperature control assembly such that a target temperature is reached, and
(iv) controllably moving the temperature control assembly and the vessel together relative to the base for a time period to allow generally uniform heat dispersion during thawing of the frozen biological material,
wherein the time period is determined based on at least the target temperature and a content volume of the biological material, and
wherein the frozen biological material comprises viable cells.

27. The method of claim 26, wherein the vessel is a vial or tube.

28. The method of claim 26, wherein the viable cells comprise placenta-derived stromal cells.

29. The method of claim 26, wherein the frozen biological material is cryopreserved.

30. The method of claim 26, further comprising halting the step of controllably moving the temperature control assembly and the vessel after the time period has elapsed.

31. The method of claim 26, further comprising terminating the step of applying heat after the time period has elapsed.

32. The method of claim 26, further comprising terminating the step of applying heat after the target temperature is reached.

33. The method of claim 26, further comprising keeping the biological material at a constant temperature after thawing.

34. The method of claim 26, further comprising recording an identifier associated with the biological material.

35. The method of claim 26, further comprising recording information associated with at least one of a temperature of the temperature control assembly, a temperature of the biological material, a speed of movement of the heating device, and the time period of said step of applying heat.

* * * * *